United States Patent
Pelletier et al.

(10) Patent No.: US 9,845,663 B2
(45) Date of Patent: Dec. 19, 2017

(54) SELF-CLEANING WINDOWS FOR DOWNHOLE AND PROCESS CHEMISTRY ENVIRONMENT

(71) Applicant: Halliburton Energy Services, Inc., Houston, TX (US)

(72) Inventors: Michael T. Pelletier, Houston, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 282 days.

(21) Appl. No.: 14/440,541

(22) PCT Filed: Apr. 2, 2014

(86) PCT No.: PCT/US2014/032634
§ 371 (c)(1),
(2) Date: May 4, 2015

(87) PCT Pub. No.: WO2015/152909
PCT Pub. Date: Oct. 8, 2015

(65) Prior Publication Data
US 2016/0290102 A1    Oct. 6, 2016

(51) Int. Cl.
*E21B 37/00* (2006.01)
*E21B 49/10* (2006.01)
*G01N 21/64* (2006.01)
*G01N 33/00* (2006.01)
*E21B 49/08* (2006.01)

(52) U.S. Cl.
CPC ............ *E21B 37/00* (2013.01); *E21B 49/081* (2013.01); *E21B 49/10* (2013.01); *G01N 21/64* (2013.01); *G01N 33/004* (2013.01); *E21B 2049/085* (2013.01); *G01N 2201/061* (2013.01)

(58) Field of Classification Search
CPC ........ E21B 37/00; E21B 49/081; E21B 49/10; E21B 2049/085; G01N 21/64; G01N 33/064; G01N 2201/061; B32B 17/10036; B32B 17/10761; B32B 17/10714; Y10T 428/252
See application file for complete search history.

(56) References Cited

U.S. PATENT DOCUMENTS

| | | |
|---|---|---|
| 5,779,912 A | 7/1998 | Gonzalez-Martin et al. |
| 6,027,766 A | 2/2000 | Greenberg et al. |

(Continued)

FOREIGN PATENT DOCUMENTS

WO    2008-152591 A1    12/2008

OTHER PUBLICATIONS

International Search Report and Written Opinion issued in related PCT Application No. PCT/US2014-032634 dated Dec. 23, 2014, 15 pages.

(Continued)

*Primary Examiner* — Yong-Suk (Philip) Ro
(74) *Attorney, Agent, or Firm* — Benjamin Fite; Baker Botts L.L.P.

(57) ABSTRACT

Methods including applying a photo-activated catalyst to a window, directing an ultraviolet light onto the window, producing a bleach via an oxidation reaction, and breaking down organic compounds located on the window using the bleach are provided. Also provided herein are systems including an ultraviolet light source and a window having a photo-activated catalyst layer.

18 Claims, 6 Drawing Sheets

(56) References Cited

U.S. PATENT DOCUMENTS

| | | |
|---|---|---|
| 6,677,063 B2 | 1/2004 | Finley |
| 7,300,166 B2 | 11/2007 | Agrawal et al. |
| 7,842,338 B2 | 11/2010 | Athey et al. |
| 8,575,541 B1 | 11/2013 | Jamison et al. |
| 2002/0043620 A1 | 4/2002 | Tchakarov et al. |
| 2005/0013750 A1 | 1/2005 | Monzyk et al. |
| 2007/0202342 A1 | 8/2007 | Whiteford et al. |
| 2009/0284259 A1 | 11/2009 | Csutak |
| 2010/0163754 A1 | 7/2010 | Van Herpen |
| 2010/0202932 A1 | 8/2010 | Danville |
| 2011/0027130 A1 | 2/2011 | Willette |
| 2013/0118734 A1 | 5/2013 | Csutak |

OTHER PUBLICATIONS

Fujishima et al., "Titanium dioxide photocatalysis", Journal of Photochemistry and Photobiology, C: Photochemistry Reviews 1 (2000) pp. 1-21.
Tachikawa et al., "Single-Molecule Fluorescence Imaging of TiO2 Photocatalytic Reactions", Langmuir 2009, 25(14), pp. 7791-7802.
Downare et al., "Visible and Near-Infrared Fluorescence of Crude Oils", Applied Spectroscopy, vol. 49, Issue 6, pp. 754-764 (1995).
International Preliminary Report on Patentability issued in related Application No. PCT/US2014/032634, dated Oct. 13, 2016 (12 pages).
Extended European Search Report issued in related European Patent Application No. 14888208.7 dated Sep. 21, 2017, 8 pages.

SELF-CLEANING WINDOWS FOR DOWNHOLE AND PROCESS CHEMISTRY ENVIRONMENT

CROSS-REFERENCE TO RELATED APPLICATION

The present application is a U.S. National Stage Application of International Application No. PCT/US2014/032634 filed Apr. 2, 2014, which is incorporated herein by reference in its entirety for all purposes.

BACKGROUND

This disclosure relates generally to optical elements located downhole in a fluid system, and more particularly concerns use of a photo-catalytic process to prevent an optical element in a wellbore fluid system from being obscured or clouded by debris or contaminants contained in the fluid stream.

The application of many downhole optical techniques requires transparent optical elements that separate a fluid to be measured or analyzed from the measurement system. It is important for optical elements, including windows, lens or lens systems, and lighting systems, to remain clear. In many optical applications, the optical elements may become dirty by various components and material contained in the fluid. An optical element that becomes clouded or obscured will prevent an optical system from performing optimally. In some applications, like downhole fluid analysis, replacement or cleaning of the optical element may be impracticable, expensive and may delay operations.

It is important to have a method to clean the optical elements in-situ or prevent them from becoming obscured in-situ without needing to raise them to the surface. A substantial amount of time may be involved in lowering an optical element into the wellbore, raising the optical element out of the wellbore for cleaning, and then lowering it again after it is cleaned. Further, in passing through fluids on the way back down, the optical element may become obscured once again.

It is desirable to provide a downhole optical system capable of measuring and analyzing downhole conditions over an extended period of time without being rendered inoperative due to the adherence of obscuring downhole fluids or the action of caustic fluids. Specifically, it is desirable to develop a process to clean optical elements downhole that is capable of withstanding high pressures and high temperatures.

BRIEF DESCRIPTION OF THE DRAWING(S)

The present disclosure will be more fully understood by reference to the following detailed description of the preferred embodiments of the present disclosure when read in conjunction with the accompanying drawings, in which like reference numbers refer to like parts throughout the views, wherein.

Figure 1:
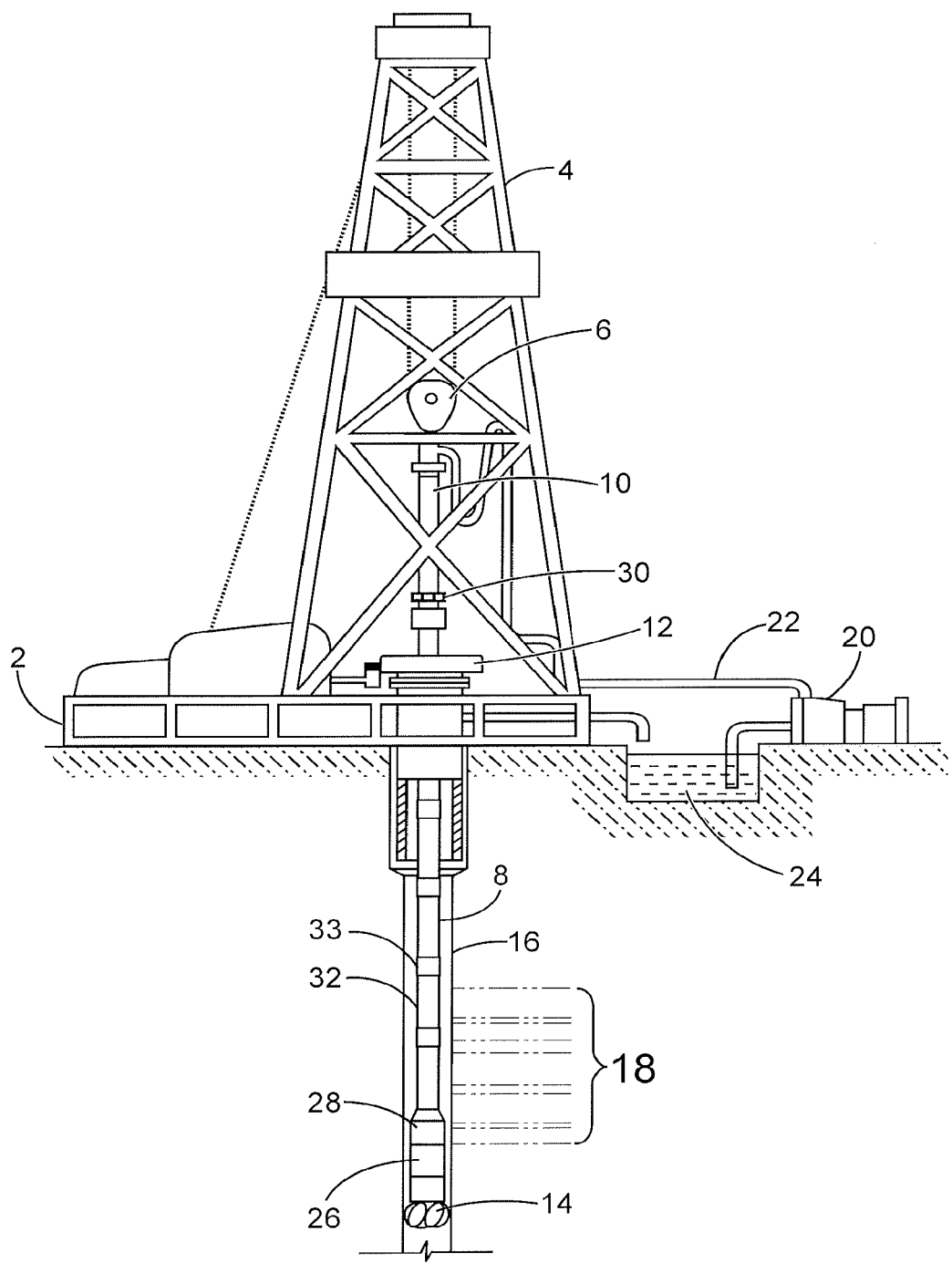
FIG. 1 depicts an illustrative logging-while-drilling (LWD) environment in accordance with one embodiment of the present disclosure.

The disclosure may be embodied in other specific forms without departing from the spirit or essential characteristics thereof. The present embodiments are therefore to be considered in all respects as illustrative and not restrictive, the scope of the disclosure being indicated by the appended claims rather than by the foregoing description, and all changes which come within the meaning and range of equivalency of the claims are therefore intended to be embraced therein.

DETAILED DESCRIPTION OF THE DISCLOSURE

Illustrative embodiments of the present invention are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

The terms "couple" or "couples," as used herein are intended to mean either an indirect or a direct connection. Thus, if a first device couples to a second device, that connection may be through a direct connection, or through an indirect electrical or mechanical connection via other devices and connections. Two elements may be "optically coupled" if light may be transmitted from or through a first element to a second element without being reflected, refracted, or otherwise redirected. The term "upstream" as used herein means along a flow path towards the source of the flow, and the term "downstream" as used herein means along a flow path away from the source of the flow. The term "uphole" as used herein means along the drillstring or the wellbore from the distal end towards the surface, and "downhole" as used herein means along the drillstring or the wellbore from the surface towards the distal end.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU), hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

It will be understood that the term "oil well drilling equipment" or "oil well drilling system" is not intended to limit the use of the equipment and processes described with those terms to drilling an oil well. The terms also encompass drilling natural gas wells or hydrocarbon wells in general. Further, such wells can be used for production, monitoring, or injection in relation to the recovery of hydrocarbons or other materials from the subsurface. This could also include geothermal wells intended to provide a source of heat energy instead of hydrocarbons. Embodiments of the present disclosure may be applicable to horizontal, vertical, deviated, or otherwise nonlinear wellbores in any type of subterranean formation.

FIG. 1 shows an illustrative logging-while-drilling (LWD) environment. A drilling platform 2 may support a derrick 4 having a traveling block 6 for raising and lowering a drill string 8. A drill string kelly 10 may support the rest of the drill string 8 as it is lowered through a rotary table 12. The rotary table 12 may rotate the drill string, thereby turning a drill bit 14. As the drill bit 14 rotates, it may create a wellbore 16 that may pass through various formations 18. A pump 20 circulates drilling fluid through a feed pipe 22 to kelly 10, downhole through the interior of drill string 8, through orifices in drill bit 14, back to the surface via the annulus around drill string 8, and into a retention pit 24. The drilling fluid transports cuttings from the wellbore 16 into the pit 24 and aids in maintaining the wellbore integrity.

Figure 4:
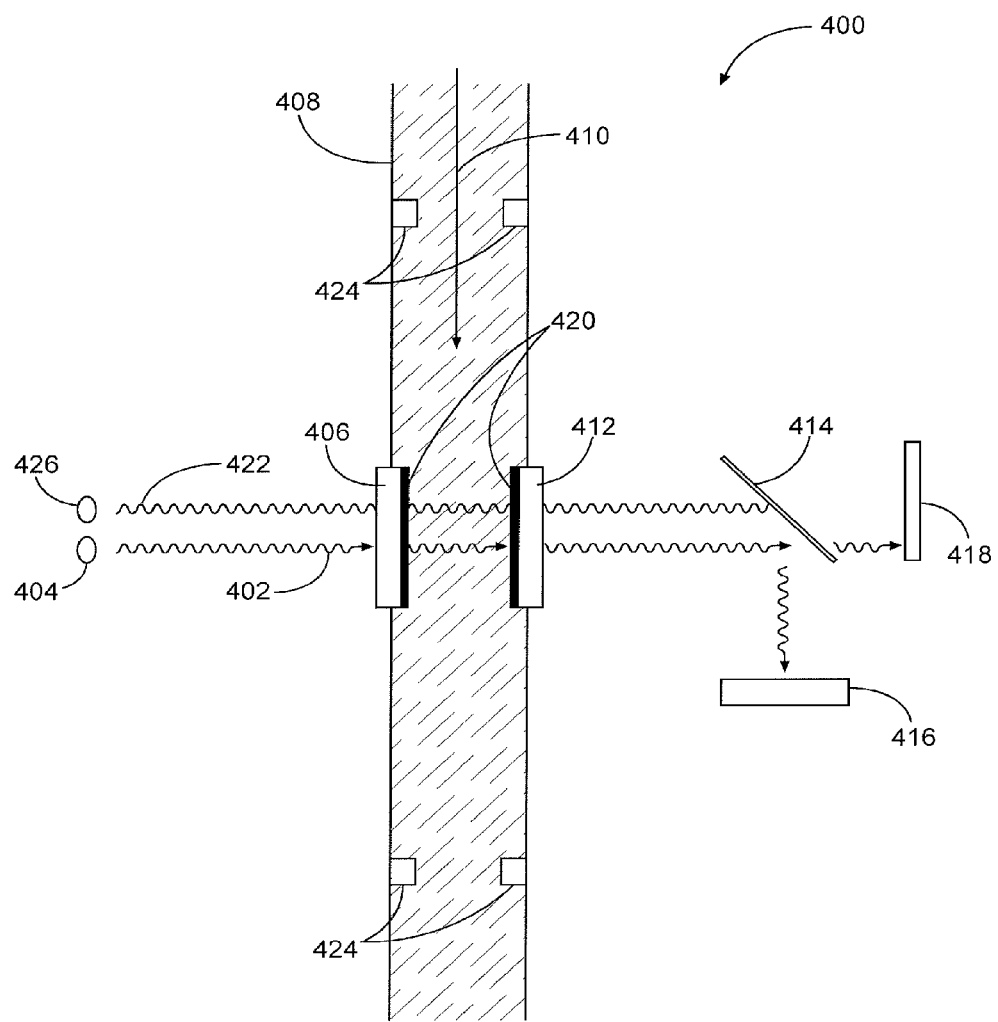
FIG. 4 depicts a system for performing optical analysis in accordance with another embodiment of the present disclosure.
Figure 5:
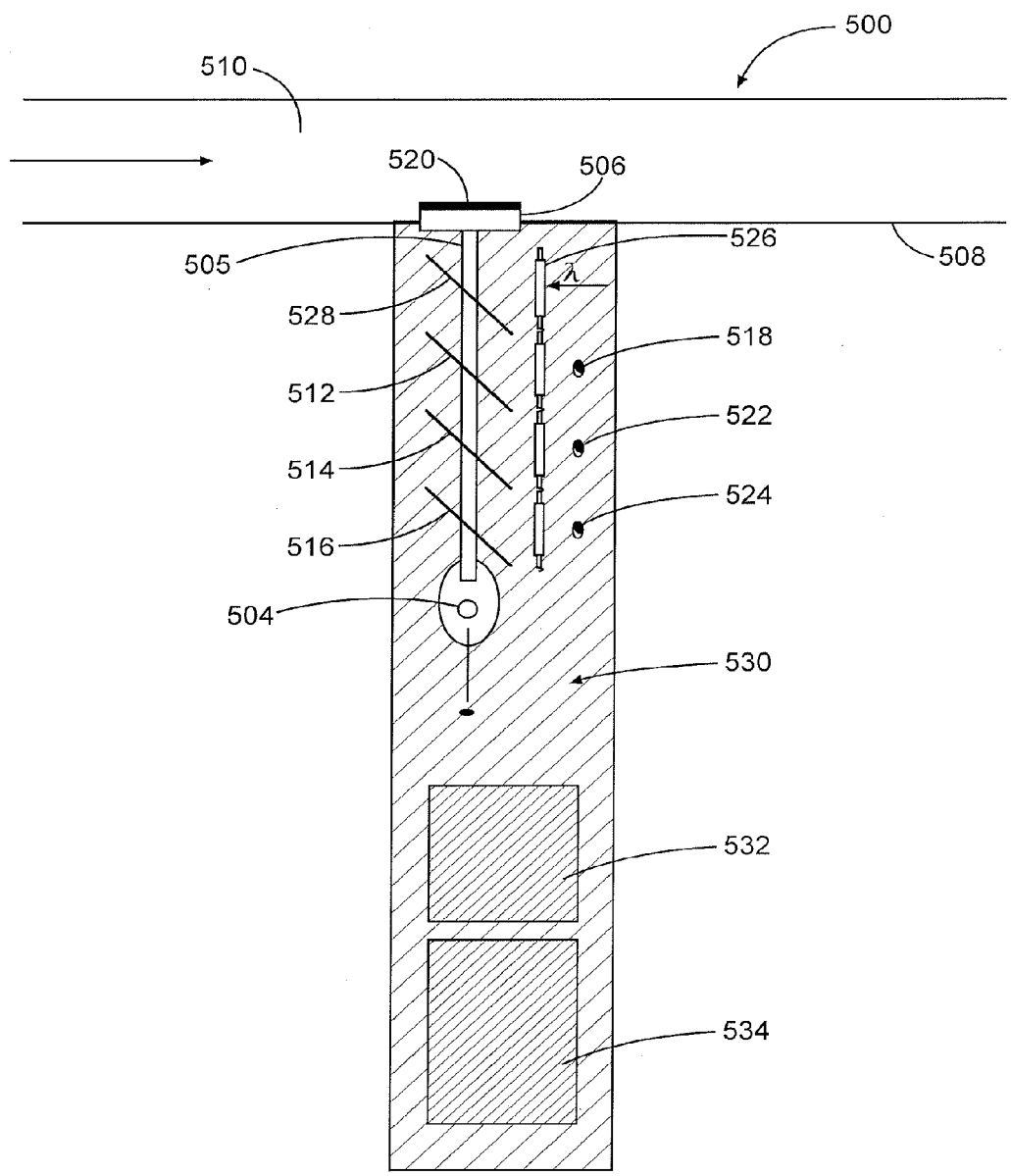
FIG. 5 depicts a system for performing optical analysis in accordance with another embodiment of the present disclosure.

The drill bit 14 is just one piece of an open-hole LWD assembly that includes one or more drill collars (thick-walled steel pipe) to provide weight and rigidity to aid the drilling process. Some of these drill collars include built-in logging instruments to gather measurements of various drilling parameters such as position, orientation, weight-on-bit, wellbore diameter, etc. As an example, a logging tool 26 (such as downhole fluid analysis tool) may be integrated into the bottom-hole assembly near the bit 14. The drill string 8 may also include multiple other sections 32 that are coupled together or to other sections of the drill string 8 by adaptors 33. In some embodiments, logging tool 26 or a section 32 may include at least one optical analysis system 400 or 500 as shown in FIG. 4 or 5.

Measurements from the tool 26 and/or other sections 32 can be stored in internal memory and/or communicated to the surface. As an example, a telemetry sub 28 may be included in the bottom-hole assembly to maintain a communications link with the surface. Mud pulse telemetry is one common telemetry technique for transferring tool measurements to surface receivers 30 and receiving commands from the surface, but other telemetry techniques can also be used.

Figure 2:
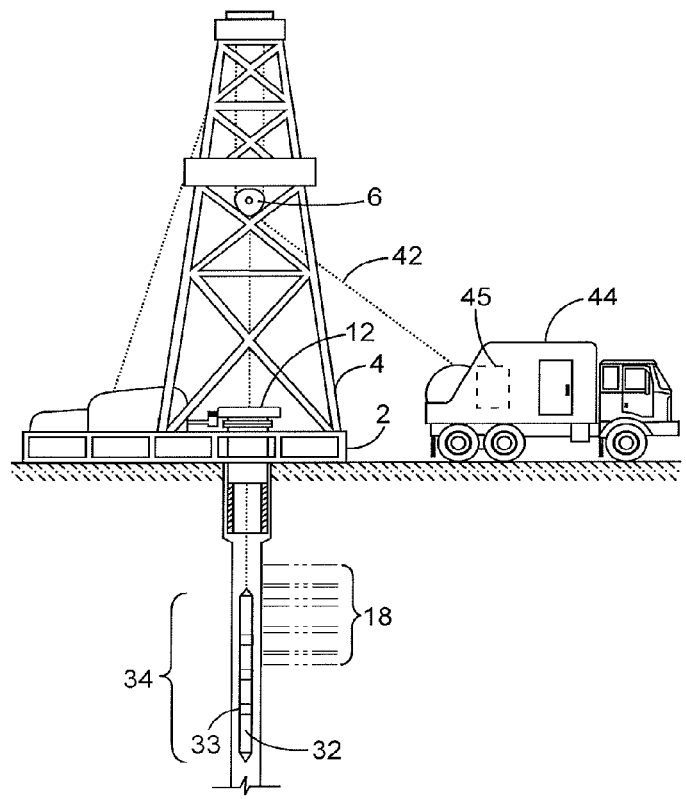
FIG. 2 depicts an illustrative wireline logging environment equipped with wireline in accordance with another embodiment of the present disclosure.

At various times during the drilling process, the drill string 8 may be removed from the wellbore 16 as shown in FIG. 2. Once the drill string has been removed, logging operations can be conducted using a wireline logging tool 34, i.e., a sensing instrument sonde suspended by a cable 42 having conductors for transporting power to the tool and telemetry from the tool to the surface. It should be noted that various types of formation property sensors can be included with the wireline logging tool 34. Without limitation, the wireline logging tool 34 includes one or more sections 32 joined by adaptors 33. In some embodiments, logging tool 34 or a section 32 may include at least one optical analysis system 400 or 500 as shown in FIGS. 4 and 5.

A logging facility 44 may collect measurements from the logging tool 34, and may include computing facilities 45 for managing logging operations and storing/processing the measurements gathered by the logging tool 34. For the logging environments of FIGS. 1 and 2, measured parameters may be recorded and displayed in the form of a log, i.e., a two-dimensional graph showing the measured parameter as a function of tool position or depth. In addition to making parameter measurements as a function of depth, some logging tools also provide parameter measurements as a function of rotational angle. With other tools, such as formation evaluation tools, the parameter logged at each depth is provided as a function of pumped volume or time.

Figure 3:
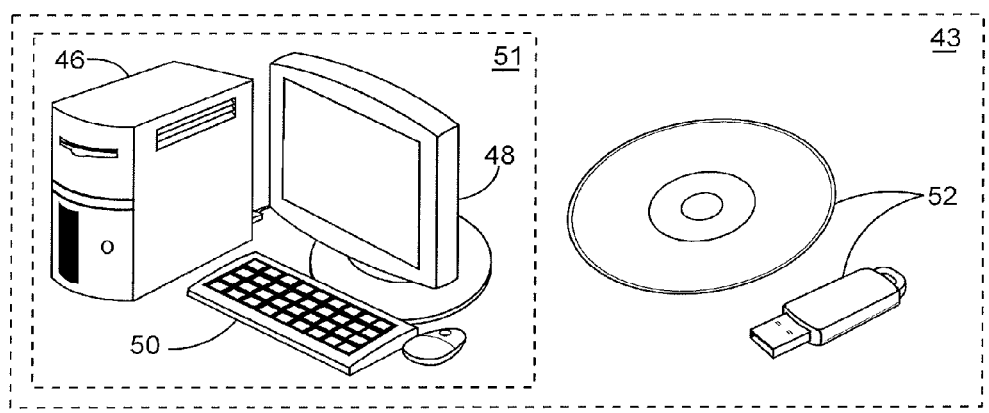
FIG. 3 depicts an illustrative information handling system for managing logging operations.

FIG. 3 shows an illustrative information handling system 43 for managing logging operations. The information handling system 43 may correspond to the computing facilities 45 of logging facility 44 (both shown in FIG. 2) or a remote computing system. The information handling system 43 may include wired or wireless communication interfaces for managing logging operations during a logging process. As shown, the information handling system 43 comprises user workstation 51, which includes a general processing system 46. The general processing system 46 is preferably configured by software, including, but not limited to, removable, non-transitory (i.e., non-volatile) information storage media 52, to manage logging operations including optical analysis operations from optical analysis systems such as 400 or 500 shown in FIGS. 4 and 5. The software may also be downloadable software accessed through a network (e.g., via the Internet). As shown, general processing system 46 may couple to a display device 48 and a user-input device 50 to enable a human operator to interact with system software stored by computer-readable media 52.

In some embodiments, software executing on the user workstation 51 may present a logging management interface with fluid analysis options to the user. Stated in another fashion, various logging management methods described herein can be implemented in the form of software that can be communicated to an information handling system or another processing system on an information storage medium such as an optical disk, a magnetic disk, a flash memory, or other persistent storage device. Alternatively, such software may be communicated to the information handling system or processing system via a network or other information transport medium. The software may be provided in various forms, including interpretable "source code" form and executable "compiled" form. The various operations carried out by the software as described herein may be written as individual functional modules (e.g., objects, functions, or subroutines) within the source code.

Referring now to FIG. 4, a system for performing optical analysis is referenced generally by reference numeral 400. A flow pipe 408 may contain a fluid 410. The flow pipe 408 may be coupled to a first and second window 406, 412. A UV light source 426 and a light source 404 may be located outside of the flow pipe 408 but may be optically coupled to the first window 406. An optical element 414 and detectors 416, 418 may be located outside of the flow pipe 408. The optical element 414 may be optically coupled to the detectors 416, 418 and to the first and second windows 406, 412.

Over time, undesirable compounds may stick or adhere to the fluid-contacted surfaces 420 of the windows 406, 412. The undesirable compounds may include, but are not limited to, debris, crude oil, mud, production fluids, asphaltenes, and organic or inorganic compounds. These compounds may cloud the fluid-contacted surfaces 420 of the windows 406, 412 and in some instances may cause the measurements of the optical element 414 and detectors 416, 418 to be inaccurate.

In accordance with an illustrative implementation of the present disclosure, the fluid-contacted surfaces 420 of the windows 406, 412 may be treated with a photo-activated catalyst (PAC) before the windows 406, 412 are installed downhole. The PAC may be a thin film, and may be applied by thin-film deposition processes like chemical vapor deposition (CVD), thermal deposition, reactive magnetron sputter vacuum deposition, or atomic layer deposition (ALD). The thickness of the PAC layer may be on the order of angstrom to microns ($10^{-10}$ m to $10^{-6}$ m). The PAC film is designed to be optically transparent at the wavelength range at which an analytical measurement is to be taken (i.e., the electromagnetic radiation 402 must be able to pass through the windows 406, 412 treated with the PAC), but may be optically opaque outside this wavelength range. The PAC may include, but is not limited to, titanium dioxide ($TiO_2$). The PAC may be applied to the windows 406, 412 as a thin film, or as a pattern. Thus, the PAC layer may be applied to the windows 406, 412.

UV light 422 may be directed from the UV light source 426. In this embodiment, UV light source 426 is selectively engaged to direct UV light 422 for cleaning purposes, and the light source 404 is engaged to direct electromagnetic radiation 402 for analytical purposes.

The UV light 422 may be directed from the UV light source 426 while light source 404 is not in use so as not to interfere with the analysis. The UV light 422 may be directed from the UV light source 426 to the first window 406. Thus, the UV light source 426 and the first window 406 may be optically coupled. Two elements may be optically coupled, for example, if light may pass from or through a first element, such as the UV light source 426, to a second element, such as the first window 406, without being reflected, refracted, or otherwise redirected by an intervening element. The UV light 422 may excite the PAC layer and, in the presence of water or hydroxyl groups, creates hydroxyl radicals ($^{\cdot}OH$) and super-oxide ions ($O_2^{-}$), which are highly reactive. The process may include, but is not limited to, peroxide ($H_2O_2$), depending on the temperature and pressure in the system. In the example that the PAC layer is a $TiO_2$ film, the UV excitation of the $TiO_2$ film by the UV light 422 may form pairs of electrons ($e^{-}$) and holes ($h^{+}$):

$$TiO_2 + 2h\nu \rightarrow 2e^{-} + 2h^{+} \quad (1)$$

Hydroxyl radicals are produced from water at $TiO_2$ by:

$$H_2O + h^{+} \rightarrow {^{\cdot}OH} + H^{3O} \quad (2)$$

Oxygen is produced by oxidation on the $TiO_2$ surface:

$$2H_2O + 4h^{+} \rightarrow O_2 + 4H^{+} \quad (3)$$

Oxygen is consumed by reduction to a bleaching agent, e.g., super-oxide or hydrogen peroxide by:

$$O_2 + e^{-} \rightarrow O2^{-} \quad (4)$$

$$O_2 + 2H^{+} + 2e^{-} \rightarrow H_2O_2 \quad (5)$$

The reaction products, including the bleaching agent, may operate to break down the undesirable compounds adhered to windows 406 and 412 to $CO_2$ and $H_2O$ and release them into the fluid 410. Excess UV light 422 may pass through the fluid 410 and may reach the second window 412, where the same process may occur.

In another embodiment of the present disclosure, the UV light source 426 may be located on the same side of the flow pipe 408 as detectors 416, 418, and ICE 414 such that the UV light 422 may be directed first at the second window 412. Thus, the location of the UV light source 426 may change without departing from the scope of this disclosure.

Electromagnetic radiation 402 may be directed from the light source 404 through a first window 406, a flow pipe 408 containing a fluid 410, and a second window 412. The electromagnetic radiation may be monochromatic or broadband radiation from wavelengths ranging from the UV to the far-infrared. The flow pipe 408 may be a casing, tubing or a sample cell. The electromagnetic radiation 402 then travels through an optical element 414 located on the opposite end of the flow pipe 408 from the light source 404. The optical element 414 may include, but is not limited to, an Integrated Computational Element (ICE) also known as a Multivariate Optical Element (MOE). The optical element 414 may utilize a thin film interference filter to sense the magnitude of a spectral pattern. A no-moving parts spectrometer highly selective to a particular analyte may be constructed by designing simple calculations based on the filter transmission and reflection spectra.

The optical element 414 may separate electromagnetic radiation 102 into components and provide an optical signal that is related to a characteristic of interest of an analyte in a sample. The optical element 414 may also include at least one of a bandpass filter or a neutral density filter. The optical element 414 may direct the electromagnetic radiation 402 to a first detector 416 and a second detector 418. The output of the first detector 418 may be a property or concentration of interest. This output may be converted to an appropriate signal for communication purposes via standard electronics. The property or concentration result, in real time, may be displayed. It may also be employed in an active feedback loop to control the property or concentration of interest or may be used to alert for certain desired conditions, such as out of range condition, or interrupted flow. The second detector 416 may be used to normalize the signal of the first detector 418 for light intensity variations, scattering effects, and the like.

In another embodiment of the present disclosure, the light source 404 may be operable to direct either electromagnetic radiation 402 or UV light 422, such that a separate UV light source 426 is not needed. A bandpass filter may be used to remove UV wavelengths from electromagnetic radiation 402 when light source 404 is operated for analytical purposes. The bandpass filter may be removed when the light source 404 is operated for cleaning purposes.

As the UV light 422 reaches the optical element 414 and is directed to the first detector 418 and second detector 416, optical monitoring may be used. Optical monitoring may help the operator monitor the cleaning process and ensure the process reaches completion. The first and second detectors 418 and 416 may be sensitive to fluorescence emission frequencies of either or both of the PAC layer or crude oil components (i.e., asphaltenes) that may have deposited on the windows 406, 412 during use. During the cleaning process, the fluorescence emission intensity will reduce or change relative to the background PAC layer as the windows 406, 412 are cleaned and flushed. The fluorescence emission intensity may be continuously detected and recorded by the detectors 416, 418 and monitored over time.

In certain embodiments, the intensity of the light 402 may also be monitored at the first detector 416. As undesirable compounds adhered to windows 406 and 412 are converted to $CO_2$, the overall intensity of the light 402 at the first detector 416 will improve.

Additionally, in certain embodiments, the level of $CO_2$ in the fluid 410 both upstream and downstream of the windows 406 and 412 may be monitored over time using, for example, sensors 424 located in the flow pipe 408. Specifically, the differential reading of the level of $CO_2$ in the fluid 410 upstream of the windows 406 and 412 versus downstream of the windows 406 and 412 may be monitored over time. The $CO_2$ monitoring may be done automatically. For example, the monitoring may be performed remotely by an information handling system remote to the sensors 424. The information handling system may receive a signal relating to the amount of $CO_2$ in the fluid 410 upstream of the windows 406 and 412 and another signal relating to the amount of $CO_2$ in the fluid 410 downstream of the windows 406 and 412. The information handling system may output a signal when the difference between those two amounts crosses a certain threshold. A positive differential reading (downstream versus upstream) may indicate the presence of additional $CO_2$ in the fluid 410 due to the decomposition of organic materials. The difference in $CO_2$ in the fluid 410 downstream of the windows 406 and 412 versus upstream of the windows 406 and 412 may approach zero when the windows are clean.

In certain embodiments, the detectors 416 and 418 may be communicatively coupled to an external communications interface (not shown). The external communications interface may permit the data from the detectors 416 and 418 to be remotely accessible by any remote information handling system communicatively coupled to the external communications interface via, for example, a satellite, a modem or wireless connections. In one embodiment, the external communications interface may include a router.

Referring now to FIG. 5, a system for performing optical analysis in accordance with a second embodiment of the present disclosure is referenced generally by reference numeral 500. FIG. 5 depicts a system in which light is sent from a light source 504 through a fiber optic light channel 505 through a window 506, a flow pipe 508 containing a fluid 510, and then is reflected back from a fluid 510 through the window 506 to one or more optical elements 512, 514, 516. The fluid 510 may have relatively high absorption of light or be a relatively opaque fluid compared to the fluid in the embodiment shown in FIG. 4. The optical elements 512, 514, 516 direct the light to one or more detectors 518, 522, 524 which may output information about the fluid 510. As in FIG. 4, the optical elements 512, 514, 516 may include, but are not limited to, an Integrated Computational Element (ICE). In some embodiments, the light source 504 may be powered by one or more on-board batteries 532. A sensor assembly 530 may be disposed adjacent to the flow pipe 508.

In the embodiment shown in FIG. 5, a UV light source 526 may operate either continuously or selectively by an operator. By operating continuously, the UV light source 526 does not interfere with the operation and measurements emanating from the light source 504 because the UV light source 526 is offset from the light source 504. The UV light source 526 may direct UV light to a beamsplitter 528 that may direct a portion of the UV light to the window 506. A beamsplitter 528 may include a mirror but is not intended to be limited to such. When the UV light reaches the fluid-contacted surface 520 of the window 506, the oxidation reactions occur as described above in connection with the embodiment of FIG. 4. In some embodiments, the sensor assembly 530 may contain on-board memory 534. Data may be sent to and stored in the on-board memory 534. As shown in FIG. 5, the sensor assembly 530 may include the window 506, the light source 504, optical elements 512, 514, 516, the detectors 518, 522, 524, the UV light source 526, the beamsplitter 528, and the batteries 532. However, this is not intended to be limiting, and the sensor assembly 530 may include a greater or fewer number of components depending on the particular embodiment.

Figure 6:
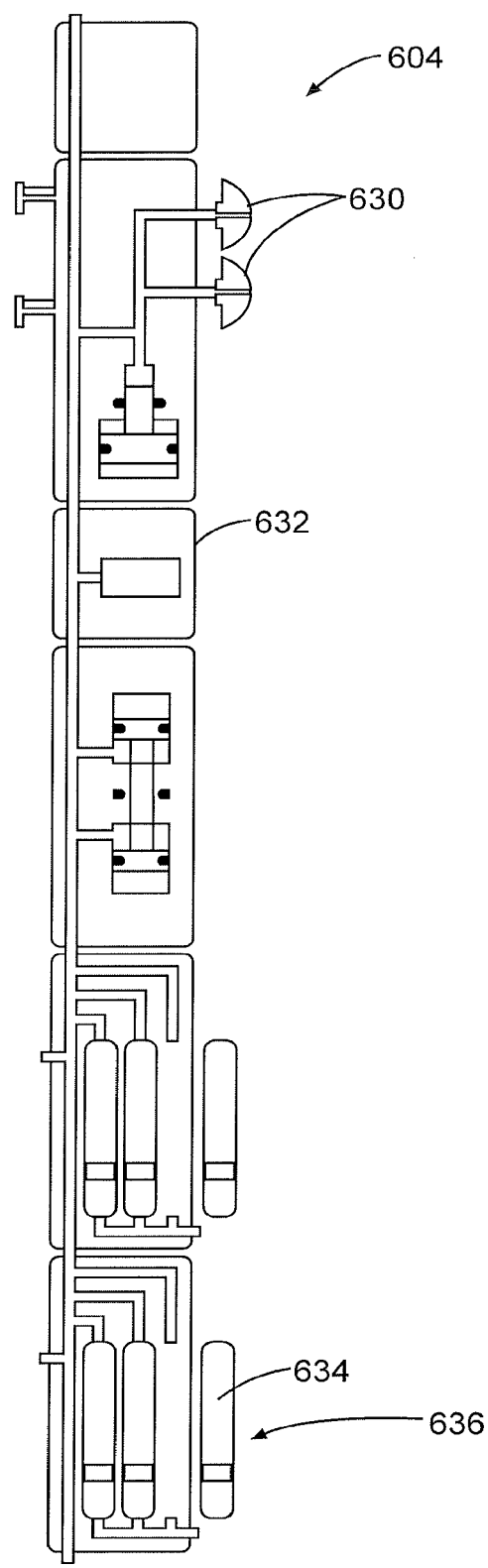
FIG. 6 depicts an illustrative wireline tool that may travel downhole to deliver cleaning fluid in accordance with another embodiment of the present disclosure.

Turning now to FIG. 6, a wireline tool 604 is shown generally. The wireline tool 604 may include a Reservoir Description Tool but is not intended to be limited to such. The wireline tool 604 may travel downhole via wireline as described in association with FIG. 2. In some situations, the fluid 410 and 510 shown in FIGS. 4 and 5 may be a gas or an oil-only fluid. Therefore, there may not be enough water in the fluid 410 or 510 to perform the reactions shown in Equations 1-5. Thus, in certain embodiments, a cleaning fluid 634 may be brought downhole in the wireline tool 604 in bottles 636 and periodically injected into the flow pipe 408 or 508. The cleaning fluid 634 may include, but is not limited to: an oxidizing solvent, an organic solvent, or an inorganic solvent, or water. The cleaning fluid 634 may travel downhole in the wireline tool 604. Oxidizing solvents may include, but are not limited to: solutions of hydrogen peroxide, persulfates, sodium permanganate, or potassium permanganate. Organic solvents may include, but are not limited to: benzene, toluene, or ethylbenzene. Inorganic solvents may include, but are not limited to: solutions of NaOH (strong base), or HCl (strong acid), depending on the system.

In operation of the wireline tool 604, the wireline tool 604 may isolate a small section of formation 18 with either packers (not shown) or a probe set 630. A group of sensors 632 may be coupled to the probe set 630. The sensors 632 may he used to locate the windows. The cleaning fluid 634 may be made to flow into the pipe 408 or 508 (shown in FIGS. 4 and 5), each of which contains windows (406 or 412, or 506). Thus, the cleaning fluid 634 may flow across the windows either in a pulsed mode or continuous mode. Under pulsed mode, the wireline tool 604 may alternate between relatively short sequences of cleaning fluid 634 and formation fluid until a window is cleaned. Optical signals as described in connection with FIGS. 4 and 5 may be used to determine when the windows are clean. Under continuous mode, cleaning fluid 634 may be sent into the pipe until the volume of cleaning fluid 634 in the bottle 636 is depleted. Again, cleanliness may be determined by comparing a clean baseline optical measurement with post-cleaning optical measurements.

In some instances there may be a desire to continuously monitor one or more chemical aspects of the fluid 410. In some instances, a wireline tool may be inappropriate for this endeavor, perhaps, for example, because of the onset of water or gas breakthrough in an enhanced recovery situation or because of the quantity of a corrosion inhibitor or some other treatment chemical which may be injected or produced in a wellbore. A wireline tool may be inappropriate because of cost, risk, or physical constraints within the wellbore.

Figure 7A:
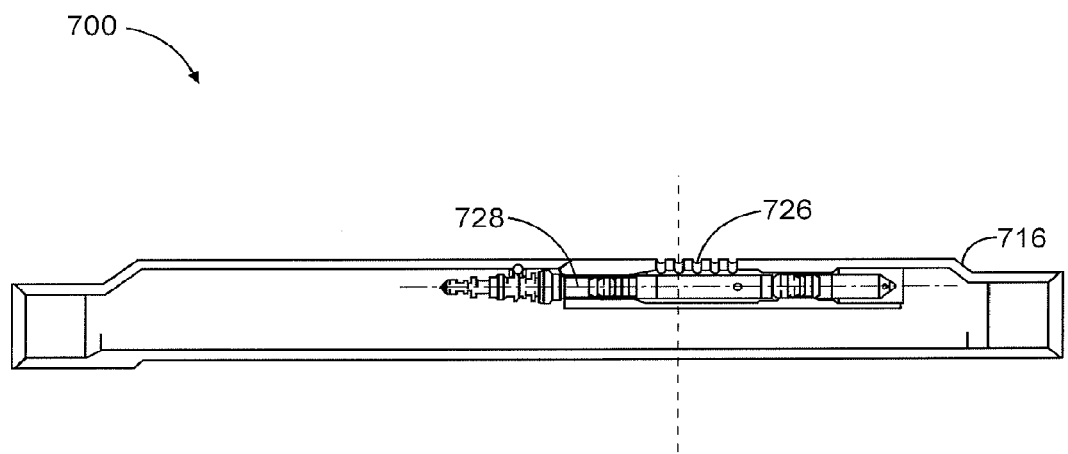
FIGS. 7A and 7B depict a section of an exemplary gas lift mandrel in accordance with another embodiment of the present disclosure.

FIG. 7A depicts a section of an exemplary gas lift mandrel 700 having a side pocket 716. The gas lift mandrel 700 may be incorporated into a string of production tubing within a wellbore. The gas lift mandrel 700 may, for example, be used to help lift hydrocarbons up a wellbore. This may be required in later years of a well's operational life.

Figure 7B:
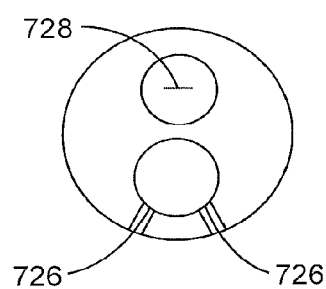

FIG. 7B depicts a cross-sectional view of the gas lift mandrel 700 shown in FIG. 7A. As illustrated in FIG. 7B, a sensor assembly 530 (shown in further detail in FIG. 5) may he disposed within a gas valve (not shown), all of which in turn may be disposed within a cavity 728 as shown in FIG. 7B. The sensor assembly 530 may include a battery 532 (shown in FIG. 5), or in some instances the gas lift mandrel 700 may be wired as part of a telemetry system and power distribution system to allow long-term well monitoring and control. The sensor assembly 530 may be designed to be serviced or retrieved by a slickline lift valve setting tool or fishing neck (not shown). The window surfaces 506 of the sensor assembly 530 may be exposed to the environment and therefore may accumulate material detrimental to the operation of the system. In such cases, the sensor assembly 530 may employ self-cleaning in a similar fashion to the systems illustrated in FIG. 5 and described in association with FIG. 5. Water or a bleaching agent may pass through ports 726 in order to reach the windows 506.

Additionally, in some instances a wellbore may be water-deficient. Fluids from the ports 726 in the side pocket mandrel 716 may be used to bring water or other cleaning solutions for activation. A small volume of liquid may be pumped down the annulus of the production tubular and the casing, driven by gas. The flow may be used to trigger the photo activation cycle. The sensor assembly 530 may be placed in a production environment downhole, may monitor a fluid parameter of the wellbore, and may operate in the window cleaning process as described in association with FIG. 5.

An embodiment of the present disclosure is a method that includes applying a photo-activated catalyst to a window, directing an ultraviolet light onto the window, producing a bleach via an oxidation reaction, and breaking down organic compounds located on the window using the bleach. Optionally the window may be located in a wellbore. Optionally the photo-activated catalyst may be titanium dioxide. Optionally the method may further include producing a florescent emission from the window, detecting the florescent emission at a detector, and monitoring the florescent emission over time. Optionally the method may further include directing electromagnetic radiation to an optical element, separating the electromagnetic radiation into two or more components, and providing an optical signal to a detector, wherein the optical signal may be related to a characteristic of interest of an analyte in a sample. Optionally the method may further include measuring the amount of carbon dioxide present at locations uphole and downhole of the window. Optionally the method may further include injecting a window cleaning fluid into a flow pipe, wherein the window may be coupled to the flow pipe. Optionally monitoring the florescent emission over time may occur at a location remote from the wellbore. Optionally the method may further include monitoring the amount of carbon dioxide present at locations uphole and downhole of the window over time.

Another embodiment of the present disclosure is a system that includes a window optically coupled to an ultraviolet light source, an ultraviolet light source operable to direct ultraviolet light onto the window, and a photo-activated catalyst layer applied to the window, wherein the photo-activated catalyst layer is optically transparent at certain wavelength ranges. The system may optionally include a light source optically coupled to the window, wherein the light source is operable to generate electromagnetic radiation, an optical element, optically coupled to the window and operable to receive electromagnetic radiation and ultraviolet light, and a detector, optically coupled to the optical element and operable to receive electromagnetic radiation. The system may optionally be located in a wellbore. Optionally the system may further include sensors located in the wellbore, wherein each of the sensors may measure an amount of carbon dioxide present in the wellbore. Optionally the sensors may be operable to measure the amount of carbon dioxide present at locations uphole and downhole of the window. Optionally the photo-activated catalyst layer may be titanium dioxide. Optionally the ultraviolet light source may be selectively operable. Optionally the window may be located between the ultraviolet light source and the optical element. Optionally the optical element may be located between the ultraviolet light source and the window. Optionally the system may further include a beamsplitter, wherein the beamsplitter is operable to direct a portion of the ultraviolet light from the ultraviolet light source to the window. Optionally the system may be located within a gas lift mandrel.

Therefore, the present disclosure is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified, and all such variations are considered within the scope and spirit of the present invention. Also, the terms in the claims have their plain, ordinary meaning unless otherwise explicitly and clearly defined by the patentee.

What is claimed is:

1. A method for maintaining a clean window for fluid analysis, the method comprising:
   applying a photo-activated catalyst to a window, wherein the window is located in a wellbore;
   directing an ultraviolet light onto the window;
   producing a bleach via an oxidation reaction; and
   breaking down organic compounds located on the window using the bleach.

2. The method of claim 1, wherein the photo-activated catalyst is titanium dioxide.

3. The method of claim 2, wherein monitoring the florescent emission over time occurs at a location remote from the wellbore.

4. The method of claim 1, further comprising:
   producing a florescent emission from the window;
   detecting the florescent emission at a detector; and
   monitoring the florescent emission over time.

5. The method of claim 1, further comprising:
   directing electromagnetic radiation to an optical element;
   separating the electromagnetic radiation into two or more components; and
   providing an optical signal to a detector, wherein the optical signal is related to a characteristic of interest of an analyte in a sample.

6. The method of claim 1, further comprising:
   measuring an amount of carbon dioxide present at locations uphole and downhole of the window.

7. The method of claim 6, further comprising:
   monitoring the amount of carbon dioxide present at locations uphole and downhole of the window over time.

8. The method of claim 1, further comprising:
   injecting a window cleaning fluid into a flow pipe, wherein the window is coupled to the flow pipe.

9. A system for maintaining a clean window for fluid analysis, the system comprising:

an ultraviolet light source, operable to direct ultraviolet light onto a window, wherein the window is located in a wellbore; and a photo-activated catalyst layer applied to the window, wherein the photo-activated catalyst layer is optically transparent at certain wavelength ranges.

10. The system of claim 9, further comprising:

a light source, optically coupled to the window, wherein the light source is operable to generate electromagnetic radiation;

an optical element, optically coupled to the window and operable to receive the electromagnetic radiation and ultraviolet light; and a detector, optically coupled to the optical element and operable to receive the electromagnetic radiation.

11. The system of claim 10, further comprising sensors located in the wellbore, wherein each of the sensors is operable to measure an amount of carbon dioxide present in the wellbore.

12. The system of claim 11, wherein the sensors are operable to measure the amount of carbon dioxide present at locations uphole and downhole of the window.

13. The system of claim 10, wherein the window is located between the ultraviolet light source and the optical element.

14. The system of claim 10, wherein the optical element is located between the ultraviolet light source and the window.

15. The system of claim 10, further comprising a beamsplitter, wherein the beamsplitter is operable to direct a portion of the ultraviolet light from the ultraviolet light source to the window.

16. The system of claim 10, wherein the system is further located within a gas lift mandrel.

17. The system of claim 9, wherein the photo-activated catalyst layer is titanium dioxide.

18. The system of claim 9, wherein the ultraviolet light source is selectively operable.

* * * * *